(12) United States Patent
Elsayed et al.

(10) Patent No.: US 11,707,504 B1
(45) Date of Patent: Jul. 25, 2023

(54) FUSION PEPTIDE INHIBITORS OF HUMAN CORONAVIRUS 229E

(71) Applicant: KING FAISAL UNIVERSITY, Al-Ahsa (SA)

(72) Inventors: Mahmoud Kandeel Elsayed, Al-Ahsa (SA); Abdullah I. Al-Mubarak, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 17/850,400

(22) Filed: Jun. 27, 2022

(51) Int. Cl.
*A61K 38/16* (2006.01)
*A61P 31/12* (2006.01)

(52) U.S. Cl.
CPC ............ *A61K 38/162* (2013.01); *A61P 31/12* (2018.01)

(58) Field of Classification Search
None
See application file for complete search history.

(56) References Cited

U.S. PATENT DOCUMENTS

| 7,956,078 B2 | 6/2011 | Hilgenfeld et al. |
| 10,975,126 B1 | 4/2021 | Elsayed et al. |
| 2008/0027006 A1 | 1/2008 | Tripet et al. |
| 2022/0119456 A1 | 4/2022 | Elsayed et al. |

FOREIGN PATENT DOCUMENTS

| CN | 107022008 A | 8/2017 |
| CN | 107245095 A | 10/2017 |
| CN | 111647048 A | 9/2020 |

OTHER PUBLICATIONS

Lawrenz et al., Clinical Infectious Diseases, 2022, 75(1):e653-661. (Year: 2022).*
Kandeel, M., et al., "Repurposing of FDA-approved antivirals, antibiotics, anthelmics, antioxidants, and cell protectives against SARS-CoV-2 papain-like protease," J. Biomol. Struct. Dyn, Jun. 2020, pp. 1-8.
Sabbah, D. A., et al., "An Updated Review on Betacoronavirus Viral Entry Inhibitors: Learning from Past Discoveries to Advance COVID-19 Drug Discovery," Current Topics in Medicinal Chemistry, 21: pp. 571-596 (2021).
Abouaitah K., et al., "Nanoformulation Composed of Ellagic Acid and Functionalized Zinc Oxide Nanoparticles Inactivates DNA and RNA Viruses," Pharmaceutics 13, 274, 10.3390/pharmaceutics13122174 (2021).
Kandeel M., et al."Discovery of new potent anti-MERS CoV fusion inhibitors," Frontiers in Pharmacology 12:685161, 10.3389/fphar.2021.685161 (2021).

* cited by examiner

*Primary Examiner* — Stacy B Chen
(74) *Attorney, Agent, or Firm* — Nath, Goldberg & Meyer; Richard C. Litman

(57) ABSTRACT

Fusion peptide inhibitors of human coronavirus 229E are provided. The fusion peptide inhibitors of HCoV-229E include peptide #1 (SEQ ID NO: 1: SLTQINTTLLD-LTYEMLSLQQVVKALNESYIDLKEL), peptide #4 (SEQ ID NO: 2: SLTQINWTLLDLTYEMESLQQVVKALNE-SYIDLKEL), and peptide #11 (SEQ ID NO: 11: SLTQINT-TLLDLEYEMRSLEEVVKKLNESYIDLKEL. The fusion peptide inhibitors of HCoV-229E may be administered to a subject in need thereof to inhibit or prevent HCoV-229E cellular entry or infection with HCoV-229E. The fusion peptide inhibitors of HCoV-229E may also be used in HCoV-229E inhibition assays.

5 Claims, 1 Drawing Sheet
Specification includes a Sequence Listing.

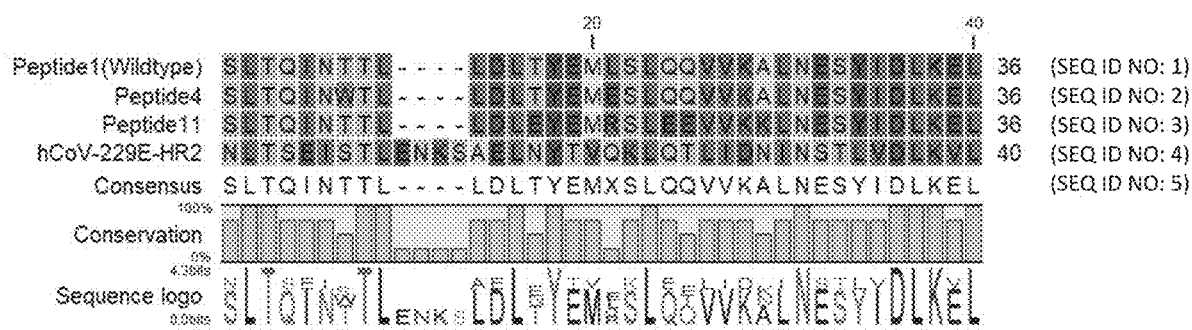

SEQUENCE LISTING

<160> NUMBER OF SEQ ID NOS: 5

<210> SEQ ID NO 1
<211> LENGTH: 36
<212> TYPE: PRT
<213> ORGANISM: Middle East Respiratory Syndrome Coronavirus

<400> SEQUENCE: 1

Ser Leu Thr Gln Ile Asn Thr Thr Leu Leu Asp Leu Thr Tyr Glu Met
1               5                   10                  15

Leu Ser Leu Gln Gln Val Val Lys Ala Leu Asn Glu Ser Tyr Ile Asp
            20                  25                  30

Leu Lys Glu Leu
        35

<210> SEQ ID NO 2
<211> LENGTH: 36
<212> TYPE: PRT
<213> ORGANISM: Middle East Respiratory Syndrome Coronavirus

<400> SEQUENCE: 2

Ser Leu Thr Gln Ile Asn Trp Thr Leu Leu Asp Leu Thr Tyr Glu Met
1               5                   10                  15

Glu Ser Leu Gln Gln Val Val Lys Ala Leu Asn Glu Ser Tyr Ile Asp
            20                  25                  30

Leu Lys Glu Leu
        35

<210> SEQ ID NO 3
<211> LENGTH: 36
<212> TYPE: PRT
<213> ORGANISM: Middle East Respiratory Syndrome Coronavirus

<400> SEQUENCE: 3

Ser Leu Thr Gln Ile Asn Thr Thr Leu Asp Leu Glu Tyr Glu Met
1               5                   10                  15

Arg Ser Leu Glu Glu Val Val Lys Lys Leu Asn Glu Ser Tyr Ile Asp
            20                  25                  30

Leu Lys Glu Leu
        35

<210> SEQ ID NO 4
<211> LENGTH: 40
<212> TYPE: PRT
<213> ORGANISM: Middle East Respiratory Syndrome Coronavirus

<400> SEQUENCE: 4

Asn Leu Thr Ser Glu Ile Ser Thr Leu Glu Asn Lys Ser Ala Glu Leu
1               5                   10                  15

Asn Tyr Thr Val Gln Lys Leu Gln Thr Leu Ile Asp Asn Ile Asn Ser
            20                  25                  30

Thr Leu Val Asp Leu Lys Val Leu
        35                  40

<210> SEQ ID NO 5
<211> LENGTH: 36
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature -continued

```
<222> LOCATION: (17)..(17)
<223> OTHER INFORMATION: Xaa may be L, E, R, or Q

<400> SEQUENCE: 5

Ser Leu Thr Gln Ile Asn Thr Thr Leu Leu Asp Leu Thr Tyr Glu Met
1               5                   10                  15

Xaa Ser Leu Gln Gln Val Val Lys Ala Leu Asn Glu Ser Tyr Ile Asp
            20                  25                  30

Leu Lys Glu Leu
        35
```

FUSION PEPTIDE INHIBITORS OF HUMAN CORONAVIRUS 229E

INCORPORATION BY REFERENCE OF MATERIAL SUBMITTED IN COMPUTER READABLE FORM

The Applicants hereby incorporate by reference the sequence listing contained in the ASCII text filed titled 32087_60U Sequence_Listing_3_ST25.txt, created Mar. 9, 2023, and having 3,825 bytes of data.

BACKGROUND

1. Field

The disclosure of the present patent application relates to biotechnology, and particularly to fusion peptide inhibitors of human coronavirus 229E ("HCoV-229E") and methods of using said peptides.

2. Description of the Related Art

The majority of coronaviruses (CoVs), including four yearly circulating human CoVs (HCoV-229E, HCoV-0C43, HCoV-NL63, and CoV-HKU1), infect animals' respiratory tracts and cause mild illness; however, zoonotic CoVs can cross the species barrier and cause epidemics in humans with significant morbidity and mortality.

The HCoV-229E virus has been associated with a variety of respiratory symptoms, ranging from the common cold to serious complications such as pneumonia and bronchiolitis which have significant morbidity rates. Significant morbidity and mortality, on the other hand, are usually seen in cases where other respiratory illnesses are present as well as the flu.

Some treatments for human coronaviruses have recently been developed. U.S. Pat. No. 10,975,126 B1 teaches MERS-CoV inhibitor peptides and their uses. However, currently, there are no approved antiviral treatments specifically targeting HCoV-229E. Symptoms are managed with traditional pain and fever medications, which do not provide any direct treatment for the viral infection.

Thus, fusion peptide inhibitors of HCoV-229E solving the aforementioned problems are desired.

SUMMARY

The fusion peptide inhibitors of HCoV-229E include peptides designed by modification or mutation of previously designed MERS-CoV inhibitor peptides. The MERS-CoV inhibitor peptides were designed by modification or mutation of a wild-type MERS-CoV fusion protein. The fusion peptide inhibitors of HCoV-229E are capable of inhibiting HCoV-229E infection in cells and may be used to prevent and/or treat HCoV-229E infection in a subject in need thereof. The HCoV-229E fusion peptide inhibitors may also be used as reagents for HCoV-229E inhibition assays as a standard or as reference inhibitors.

An embodiment of the present subject matter is directed to methods of inhibiting HCoV-229E infection, preventing HCoV-229E transmission, and/or treating a HCoV-229E infection, including administering to a subject in need thereof a therapeutically effective amount of a pharmaceutical composition comprising one or more HCoV-229E fusion peptide inhibitors. In a further embodiment, the methods of inhibiting HCoV-229E infection may include preventing HCoV-229E infection of a cell.

An embodiment of the present subject matter is directed to methods of using the HCoV-229E fusion peptides as reference agents to evaluate inhibition by other candidates against HCoV-229E. These methods may include using the HCoV-229E fusion peptides as reference agents in Cell-Cell Fusion Assays, Viral Plaque Formation Assays, Viral RNA Quantitation Assays, or the like.

These and other features of the present subject matter will become readily apparent upon further review of the following specification.

BRIEF DESCRIPTION OF THE DRAWINGS

FIG. 1 depicts an alignment of MERS-CoV inhibitor peptides 1, 4, and 11 against the HCoV-229E-HR2 Protein. In the consensus sequence, the "X" amino acid at position 17 may represent L, E, R, or Q.

Similar reference characters denote corresponding features consistently throughout the attached drawings.

DETAILED DESCRIPTION OF THE PREFERRED EMBODIMENTS

The present teachings are directed to the use of fusion peptides that are capable of inhibiting HCoV-229E infection in cells and preventing and/or treating HCoV-229E infection in a subject in need thereof. The fusion peptide inhibitors of HCoV-229E may also be used as reagents for HCoV-229E inhibition assays as a standard or as reference inhibitors.

In an embodiment, the HCoV-229E inhibition assays include a cell-cell fusion assay.

Throughout this application, the term "about" may be used to indicate that a value includes the standard deviation of error for the composition, device or method being employed to determine the value.

The use of the term "or" in the specification and claim(s) is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps. In certain cases, the term "comprising" may be replaced with "consisting essentially of" or "consisting of."

The use of the word "a" or "an" when used herein in conjunction with the term "comprising" in the claims and/or the specification may mean "one," but it is also consistent with the meaning of "one or more," "at least one," and "one or more than one."

The phrase "pharmaceutically acceptable," as used herein, refers to molecular entities and compositions that do not produce an allergic or similar untoward reaction when administered to a human.

The term "subject," as used herein, means a mammal, including but not limited to a human being.

As used herein, the term "providing" an agent is used to include "administering" the agent to a subject.

As used herein, a "carrier" includes any and all solvents, dispersion media, vehicles, coatings, diluents, isotonic and absorption delaying agents, buffers, carrier solutions, suspensions, colloids, excipients, and the like.

Pharmaceutical compositions comprising one or more of the fusion peptide inhibitors of HCoV-229E and a pharmaceutically acceptable carrier may be made using any technique generally known in the art.

As a non-limiting example, a method of making a pharmaceutical composition includes mixing one or more of the fusion peptide inhibitors of HCoV-229E with a pharmaceutically acceptable carrier. For example, the method of making a pharmaceutical composition can include mixing a fusion peptide inhibitor of HCoV-229E under sterile conditions with a pharmaceutically acceptable carrier with preservatives, buffers, and/or propellants to create the pharmaceutical composition.

As a further example, pharmaceutical compositions including fusion peptide inhibitors of HCoV-229E may be made as follows: one or more of the fusion peptide inhibitors of HCoV-229E, as the active ingredient, is intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. One or more of the fusion peptide inhibitors of HCoV-229E can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose. A therapeutically effective amount of a fusion peptide inhibitor of HCoV-229E or an amount effective to treat a disease, such as a coronavirus infection, may be determined initially from the Examples described herein and adjusted for specific targeted diseases using routine methods.

An embodiment of the present subject matter is directed to compositions including one or more of the fusion peptide inhibitors of HCoV-229E and one or more expression systems. The expression system may be a viral-based expression system, a plasmid-based expression system, or any other expression system suitable for causing or enhancing expression of the fusion peptide inhibitors of HCoV-229E in a bacterium, yeast, or mammalian cell. The expression system may include a promoter sequence and DNA or RNA encoding one or more of the fusion peptide inhibitors of HCoV-229E.

An embodiment of the present subject matter is directed to methods of using the fusion peptide inhibitors of HCoV-229E as reference agents to evaluate inhibition by other candidates against HCoV-229E. These methods may include using the fusion peptide inhibitors of HCoV-229E as reference agents in Cell-Cell Fusion Assays, Viral Plaque Formation Assays, Viral RNA Quantitation Assays, or the like.

The fusion peptide inhibitors of HCoV-229E can be administered to a subject in need thereof. In an embodiment, the fusion peptide inhibitors of HCoV-229E can be administered to a subject in need thereof to inhibit HCoV-229E infection, prevent HCoV-229E transmission, and/or treat a HCoV-229E infection.

An embodiment of the present subject matter is directed to a method of inhibiting HCoV-229E infection, preventing HCoV-229E transmission, and/or treating a HCoV-229E infection, comprising administering to a subject in need thereof a therapeutically effective amount of the pharmaceutical composition according to the present subject matter.

The fusion peptide inhibitors of HCoV-229E or pharmaceutical compositions thereof can be administered to a subject by any suitable route. For example, the compositions can be administered nasally, rectally, intracisternally, intraperitoneally, transdermally (as by powders, ointments, or drops), and/or parenterally. As used herein, "parenteral" administration refers to modes of administration other than through the gastrointestinal tract, which include intravenous, intramuscular, intraperitoneal, intrasternal, intramammary, intraocular, intrapulmonary, intrathecal, subcutaneous and intraarticular injection and infusion. Surgical implantation may also be contemplated, including, for example, embedding a composition of the disclosure in the body such as, for example, in a tissue, in the abdominal cavity, under the splenic capsule, brain, or in the cornea.

Accordingly, the route of administration can include intranasal administration, oral administration, inhalation administration, subcutaneous administration, transdermal administration, intradermal administration, intra-arterial administration with or without occlusion, intracranial administration, intraventricular administration, intravenous administration, buccal administration, intraperitoneal administration, intraocular administration, intramuscular administration, implantation administration, topical administration, intratumor administration, and/or central venous administration.

The CoV genome encodes four structural proteins: spike (S), membrane (M), envelope (E), and nucleocapsid (N). Viral membrane fusion is an essential step of virus replication, which is accomplished by the viral spike and leads to the fusion of the viral and cell membranes. The CoV S protein is composed of two subunits, S1 and S2. S1 binds the host cell ACE2 receptor. Cleavage of S1 by host cell proteases exposes a highly hydrophobic membrane-binding domain of the S2 subunit. The S2 subunit contains two domains, heptad repeat domain 1 (HR1) and heptad repeat domain 2 (HR2). HR1 forms a homotrimer exposing three hydrophobic pockets on its surface, which host the HR2 domain during the active fusion process. An HR domain is composed of tandem repeat motifs of seven residues (named a-g). Of the seven residues, the first (a) and fourth (d) are predominantly hydrophobic or bulky.

The fusion peptide inhibitors of HCoV-229E are designed by modification or mutation of a surface structure protein of MERS-CoV in the virus S2 spike region. The heptad repeat regions (HR1 and HR2) of S2 interact to help in fusion of MERS-CoV with cell membranes. The MERS-CoV inhibitor peptide S2 HR2 derivatives were optimized to interfere with the proper mechanism of HR1-HR2 interactions.

In an embodiment, the fusion peptide inhibitors of hCoV-229E include peptide #1 (SEQ ID NO: 1: SLTQINTTLLD-LTYEMLSLQQVVKALNESYIDLKEL), peptide #4 (SEQ ID NO: 2: SLTQINWTLLDLTYEMESLQQVVKALNE-SYIDLKEL), and peptide #11 (SEQ ID NO: 3: SLTQINT-TLLDLEYEMRSLEEVVKKLNESYIDLKEL).

The following examples illustrate the present subject matter.

EXAMPLE 1

Designing Peptide Inhibitors of HCoV-229E

To test the possible extended-spectrum efficacy, the sequences of previously developed MERS-CoV inhibitor peptides 1, 4 and 11 (See U.S. Pat. No. 10,975,126 and Table 1) were matched with the HCoV-229E-HR2 protein (See FIG. 1). There were some conserved residues to be found. Furthermore, the hydrophobic residues that constitute the helical component were conserved among the examined peptide sequences, with the hydrophilic residues having the largest differences. In both the MERS-CoV inhibitor peptides and HCoV-229E-HR2, the interface residues between the fusion core proteins HR1 and HR2 were predominantly conserved. This finding served as a precursor to investigating the wider spectrum of peptides 1, 4, and 11 for HCoV-229E inhibition.

TABLE 1

Peptide Sequences

| Name | Peptide Sequence | '126 SEQ ID |
|---|---|---|
| Peptide 1 (WT) | SLTQINTTLLDLTYEMLSLQQVVKALNESYIDLKEL (SEQ ID NO: 1) | 1 |
| Peptide 4 | SLTQINWTLLDLTYEMESLQQVVKALNESYIDLKEL (SEQ ID NO: 2) | 4 |
| Peptide 11 | SLTQINTTLLDLEYEMRSLEEVVKKLNESYIDLKEL (SEQ ID NO: 3) | 11 |

To get insights into the calculated values of similarity and differences between peptides 1, 4 and 11 and HCoV-229E-HR2, pairwise sequence comparison statistics were performed. Table 2 illustrates four gaps allocated in the HCoV-229E-HR sequence and 30-32.5% similarity between the MERS-CoV peptides and HCoV-229E-HR2.

TABLE 2

Pairwise Comparison Statistics

| | 1 | 2 | 3 | 4 |
|---|---|---|---|---|
| Peptide 1 (Wildtype) | | 0 | 0 | 4 |
| Peptide 4 | 94.4444 | | 0 | 4 |
| Peptide 11 | 86.1111 | 83.3333 | | 4 |
| HCoV-229E-HR2 | 32.5000 | 32.5000 | 30.0000 | |

EXAMPLE 2

Antiviral Assay

A plaque reduction test was performed as previously reported (AbouAitah, K., et al., "Nanoformulation Composed of Ellagic Acid and Functionalized Zinc Oxide Nanoparticles Inactivates DNA and RNA Viruses," Pharmaceutics 13, 274, 10.3390/pharmaceutics13122174 (2021)). Vero E6 cells were grown on a six-well plate for 24 hours at 37° C. In parallel to the untreated viral control, the virus was incubated for 30 minutes with various dilutions of the peptides. The cells were injected with (100 µl/well) countable virus/sample mixes after the growth media was withdrawn from the cell culture plates. After 1 hour of virus adsorption, 1.5 ml of DMEM supplemented with 2% agarose was added to the cell monolayer; plates were allowed to harden and incubated at 37° C. for 3 days. Formalin 10% was applied to the plates for two hours before staining with 0.1 percent crystal violet in distilled water. Untreated virus was incubated with Vero E6 cells in control wells, and plaques were enumerated. The decrease in plaque formation in comparison to control wells was calculated using Formula 1:

$$\% \text{ inhibition} = \frac{\text{viral count (untreated)} - \text{viral count (treated)}}{\text{viral count (untreated)}} \quad \text{Formula 1}$$

All three peptides 1, 4, and 11 demonstrated inhibition of HCoV-229E with $IC_{50}$ values of 8.497, 11.54, and 6.63 µg/ml respectively. (See Table 3)

TABLE 3

Inhibitory Properties of Tested Peptides Against HCoV-229E

| Peptide # | Conc. µg/ml | PFU/ml | Titer Post-Tx | Viral Inhibition % | $IC_{50}$ µg/ml |
|---|---|---|---|---|---|
| Peptide 1 | 100 | $0.036 \times 10^3$ | $0.015 \times 10^3$ | 58.3 | |
| Peptide 1 | 10 | $0.036 \times 10^3$ | $0.021 \times 10^3$ | 41.7 | 8.497 |
| Peptide 1 | 1 | $0.036 \times 10^3$ | $0.030 \times 10^3$ | 13.9 | |
| Peptide 4 | 100 | $0.036 \times 10^3$ | $0.0053 \times 10^3$ | 85.3 | |
| Peptide 4 | 10 | $0.036 \times 10^3$ | $0.0234 \times 10^3$ | 35.1 | 11.54 |
| Peptide 4 | 1 | $0.036 \times 10^3$ | $0.0352 \times 10^3$ | 2.1 | |
| Peptide 11 | 100 | $0.032 \times 10^3$ | $0.017 \times 10^3$ | 46.8 | |
| Peptide 11 | 10 | $0.032 \times 10^3$ | $0.019 \times 10^3$ | 40.6 | 6.63 |
| Peptide 11 | 1 | $0.032 \times 10^3$ | $0.029 \times 10^3$ | 9.4 | |

The conserved and common target site in the spike (S) proteins of HCoVs is essential for viral attachment and entry into the host cell. S2's heptad repeat domains HR1 and HR2 are necessary for viral fusion to create a six-helix bundle (6-HB) core structure, and they are highly conserved. The observed anti-HCOV-229E activity of MERS-CoV peptides is attributable to the conserved hydrophobic interface between HR and HR2 in both MERS-CoV and HCOV-229E fusion cores.

It is to be understood that the fusion peptide inhibitors of human coronavirus 229E are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of inhibiting human coronavirus 229E infection of a cell comprising administering a composition comprising at least one peptide having an amino acid sequence selected from the group consisting of SEQ ID NO: 1, SEQ ID NO: 2, and SEQ ID NO: 3, and a combination of two or more sequences thereof to a subject in need thereof.

2. The method of claim 1, comprising a peptide having the amino acid sequence of SEQ ID NO: 1.

3. The method of claim 1, comprising a peptide having the amino acid sequence of SEQ ID NO: 2.

4. The method of claim 1, comprising a peptide having the amino acid sequence of SEQ ID NO: 3.

5. A method for conducting a human coronavirus 229E inhibition assay comprising using at least one peptide having an amino acid sequence selected from the group consisting of SEQ ID NO: 1, SEQ ID NO: 2, and SEQ ID NO: 3 as a standard or as a reference inhibitor, wherein the assay is either a cell-cell fusion assay or a human coronavirus 229E plaque formation assay.

* * * * *